United States Patent
Ding et al.

(10) Patent No.: US 10,442,811 B2
(45) Date of Patent: Oct. 15, 2019

(54) CRYSTAL FORM A OF 2-BUTOXY-7-(4-(PYRROLIDIN-1-YLMETHYL)BENZYL)-5H-PYRROLO[3,2-D] PYRIMIDIN-4-AMINE, PREPARATION PROCESS AND USE THEREOF

(71) Applicant: CHIA TAI TIANQING PHARMACEUTICAL GROUP CO., LTD., Jiangsu, Lianyungang (CN)

(72) Inventors: Zhaozhong Ding, Shanghai (CN); Fei Sun, Shanghai (CN); Yinghu Hu, Shanghai (CN); Yilong Zhou, Shanghai (CN); Zheng Wang, Shanghai (CN); Rui Zhao, Lianyungang (CN); Ling Yang, Lianyungang (CN)

(73) Assignee: CHIA TAI TIANQING PHARMACEUTICAL GROUP CO., LTD., Jiangsu, Lianyungang (CN)

( * ) Notice: Subject to any disclaimer, the term of this patent is extended or adjusted under 35 U.S.C. 154(b) by 0 days.

(21) Appl. No.: 16/075,297

(22) PCT Filed: Feb. 4, 2017

(86) PCT No.: PCT/CN2017/072891
§ 371 (c)(1),
(2) Date: Aug. 3, 2018

(87) PCT Pub. No.: WO2017/133684
PCT Pub. Date: Aug. 10, 2017

(65) Prior Publication Data
US 2019/0040071 A1    Feb. 7, 2019

(30) Foreign Application Priority Data
Feb. 5, 2016    (CN) .......................... 2016 1 0082029

(51) Int. Cl.
*A61K 31/519*    (2006.01)
*C07D 487/04*    (2006.01)

(52) U.S. Cl.
CPC .......... *C07D 487/04* (2013.01); *A61K 31/519* (2013.01); *C07B 2200/13* (2013.01)

(58) Field of Classification Search
CPC .......................... A61K 31/519; C07D 487/04
USPC ........................................ 514/265.1; 544/280
See application file for complete search history.

(56) References Cited

U.S. PATENT DOCUMENTS

2010/0143301 A1    6/2010 Desai et al.

FOREIGN PATENT DOCUMENTS

| CA | 3013518 | * | 8/2017 |
|---|---|---|---|
| CL | 2016002751 A1 | | 12/2016 |
| CL | 2017000379 A1 | | 4/2018 |
| CL | 2018002089 A1 | | 12/2018 |
| CN | 104780923 A | | 7/2015 |
| CN | 104780924 A | | 7/2015 |
| CN | 104837840 A | | 8/2015 |
| CN | 105367576 A | | 3/2016 |
| CN | 104780924 B | | 9/2016 |
| CN | 104780923 B | | 3/2017 |
| CN | 104837840 B | | 8/2017 |
| WO | WO-2015/168269 A1 | | 11/2015 |
| WO | WO-2016/023511 A1 | | 2/2016 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report and Written Opinion, dated May 10, 2017, issued in corresponding International Application No. PCT/CN2017/072891.
Lanford, et al., "GS-9620, an Oral Agonist of Toll-Like Receptor-7, Induces Prolonged Suppression of Hepatitis B Virus in Chronically Infected Chimpanzees", Gastroenterology 144: 1508-1517 (2013).
Powder XRD, Journal of Visualized Experiments, 3 pages (2017) [Retrieved from https://www.jove.com/science-education/10462].
Remington, The Science and Practice of Pharmacy, 21st Ed., Ch. 39-42, 89 pages (2005).
Sauder, "Imiguimod: modes of action", British Journal of Dermatology 149(Suppl. 66): 5-8 (2003).
Single-Crystal versus Powder Diffraction, 3 pages [Retrieved on Apr. 29, 2019 from http://pd.chem.ucl.ac.uk/pdnn/symm4/crystal.htm].
Stout, et al., X-Ray Structure Determination, 2nd. Ed., Ch. 3, 21 pages (1989).
Wu, et al., "Resiquimod: a new immune response modifier with potential as a vaccine adjuvant for Th1 immune responses", Antiviral Research 64: 79-83 (2004).
XIX C Chinese Pharmacopoeia, pp. 199-201.
Supplementary European Search Report, issued in European Patent Appln. No. 17747004.4 (Jun. 14, 2019).
Chilean Office Action, issued in corresponding Chilean Pat. App. No. 201802092, 14 pages (Jun. 12, 2019).

* cited by examiner

Primary Examiner — Douglas M Willis
(74) Attorney, Agent, or Firm — Foley & Lardner LLP (57) ABSTRACT

The present invention relates to crystalline form A of a TLR7 agonist 2-butoxy-7-(4-(pyrrolidin-1-ylmethyl)-benzyl)-5H-pyrrolo[3,2-d]pyrimidin-4-amine (formula I), a method for preparing the crystalline form A, and the use thereof.

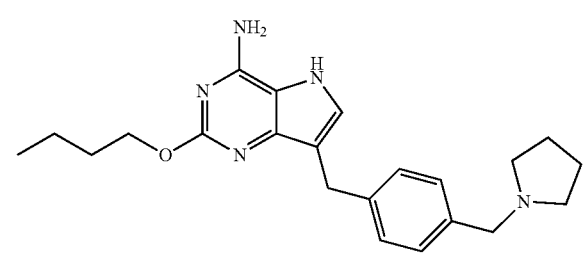

20 Claims, 2 Drawing Sheets

CRYSTAL FORM A OF 2-BUTOXY-7-(4-(PYRROLIDIN-1-YLMETHYL)BENZYL)-5H-PYRROLO[3,2-D] PYRIMIDIN-4-AMINE, PREPARATION PROCESS AND USE THEREOF

CROSS-REFERENCE TO RELATED APPLICATIONS

This application is a national phase of International Application No. PCT/CN2017/072891, filed on Feb. 4, 2017, which claims priority to Chinese Patent Application No. 201610082029.8, filed on Feb. 5, 2016, each of which is incorporated herein by reference in its entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON COMPACT DISC

Not Applicable

BACKGROUND OF THE INVENTION

(1) Field of the Invention

The present invention relates to the field of medicinal chemistry, and particularly relates to crystal form A of a TLR7 agonist (2-butoxy-7-(4-(pyrrolidin-1-ylmethyl)benzyl)-5H-pyrrolo[3,2-d]pyrimidin-4-amine), a preparing process thereof, a crystalline composition comprising the crystal form A, a pharmaceutical composition comprising the crystal form A or the crystalline composition and use thereof.

(2) Description of Related Art

Toll-like receptor is expressed by various immune cells and recognizes high reserved structural motifs: Pathogen Associated Molecular Pattern (PAMP) expressed by microorganism pathogens or Damage Associated Molecular Patterns (DAMP) released by dead cells. PAMP or DAMP stimulates Toll-like receptor to trigger signal cascade which induces the activations of transcriptional factors like AP-1, NF-κB and interferon regulators (pulse response function). It results in various cell responses, including productions of interferons, proinflammatory cytokines and effector cytokines, whereby immune response is produced. By far, 13 types of Toll-like receptors have been discovered in mammal. Toll-like receptors 1, 2, 4, 5 and 6 are mainly expressed on the cell surface while Toll-like receptors 3, 7, 8 and 9 are expressed in the endosome. Different Toll-like receptors recognize ligands derived from different pathogens. Toll-like receptor 7 (TLR7) is mainly expressed by plasmaeytoid dendritic cells (pDC), and recognized via ligand to induce the secretion of interferon α (IFN-α). Toll-like receptor 7 (TLR7) and Toll-like receptor 8 (TLR8) are highly homologous and therefore the ligand of TLR7 in most cases is also that of TLR8. TLR8 stimulation mainly induces the productions of cytokines like tumor necrosis factor α (TNF-α) and chemoattractant. Interferon α is one of the medicines for treating chronic hepatitis B or hepatitis C while TNF-α is a proinflammatory cytokine, of which the over secretion will result severe side effects.

There have been reported several TLR7 agonists, like imiquimod (British Journal of Dermatology 2003; 149 (Suppl. 66): 5-8), resiquimod (Antiviral Research 64 (2004) 79-83), GS-9620 (Gastroenterology (2013), 144(7), 1508-1517). Nevertheless, it is desirable to have novel TLR7 agonists with better selectivity, activity and safety.

Chinese Patent Application No. 201410405136.0 which is incorporated in its entirety by reference herein discloses one small molecule, i.e. 2-butoxy-7-(4-(pyrrolidin-1-ylmethyl) benzyl)-5H-pyrrolo[3,2-d]pyrimidin-4-amine, which has the following structure:

I

BRIEF SUMMARY OF THE INVENTION

In an aspect, provided is crystal form A of the compound of formula I:

I

The crystal form A is characterized by an X-ray powder diffraction (XRPD) pattern having diffraction peaks at 2θ=5.5°±0.2°, 10.1°±0.2°, 13.8°±0.2°, 19.7°±0.2°, 23.7°±0.2°, 24.1°±0.2°.

In another aspect, provided is a process for preparing crystal form A of the compound of formula I, comprising the following steps:

1) dissolving the compound of formula I in a crystallizing solvent, which is preferably heated to promote dissolution; and 2) cooling for crystallization, filtrating, washing and drying to obtain the crystal form A.

In another aspect, provided is a pharmaceutical composition, comprising the crystal form A or the crystalline composition thereof according to the invention. The pharmaceutical composition can further optionally comprise pharmaceutically acceptable carrier, excipient and/or medium.

In another aspect, provided is a method for treating or preventing Toll-like receptor 7 (TLR7) associated disease, comprising administering to a subject in need thereof the crystal form A or the crystalline composition thereof or the pharmaceutical composition according to the invention in an effective amount. Preferably, the disease is virus infection.

In a further aspect, provided is use of the crystal form A or the crystalline composition thereof or the pharmaceutical composition according to the invention for the manufacture of a medicament for treating or preventing Toll-like receptor 7 (TLR7) associated disease. Preferably, the disease is virus infection.

In a yet further aspect, provided is the crystal form A or the crystalline composition thereof or the pharmaceutical composition according to the invention for use in treating or preventing Toll-like receptor 7 (TLR7) associated disease. Preferably, the disease is virus infection.

In one embodiment of the invention, the virus infection is hepatitis virus infection, particularly hepatitis B or hepatitis C virus infection.

DETAILED DESCRIPTION OF THE INVENTION

General Definition and Terminology

Unless stated otherwise, the terms and phrases used herein have the following meaning. A specific term or phrase shall not be considered as unclear or indefinite when it is not specifically defined. It should be understood according to the general meaning. The trade name used herein refers to the corresponding product or the active ingredient.

Unless specifically defined otherwise, proportion (including percentage) or part is calculated based on weight herein.

When used with a numerical variable, the term "approximate" or "about" usually refers to the value of the variable and all the values of the variable within the experimental error (for example, within an average 95% confidence interval) or within ±10% of the specified value, or a wider range.

The expression "comprise" or its synonyms "contain", "include", "have" or the like is open-ended, which does not exclude other unlisted elements, steps or ingredients. The expression "consist of" excludes any unlisted elements, steps or ingredients. The expression "substantially consist of" refers to specified elements, steps or ingredients within a given range, together with optional elements, steps or components which do not substantively affect the basic and novel feature of the claimed subject matter. It should be understood that the expression "comprise" encompasses the expressions "substantially consist of" and "consist of".

The term "optional" or "optionally" means the event described subsequent thereto may or may not happen. This term encompasses the cases that the event may or may not happen.

The term "pharmaceutical composition" refers to an active ingredient, which is optionally combined with one or more pharmaceutically acceptable components (for example, but not limited to carrier and/or excipient). The active ingredient is exemplified as the compound of formula I or salt thereof, the crystal form according to the invention, or the crystalline composition according to the invention.

The term "pharmaceutically acceptable carrier" refers to those carriers which have no significant irritation and do not impair the bioactivity and property of the active compound. The "pharmaceutically acceptable carrier" refers to inert substance which is administered with active ingredient and is beneficial to the administration thereof, and comprises but not limited to any of the following substances approved by State Food and Drug Administration for use in human or animal (e.g. livestock): glidant, sweetening agent, diluent, preservative, dye/colorant, flavoring agent, surfactant, wetting agent, dispersant, disintegrant, suspending agent, stabilizing agent, isotonic agent, solvent or emulsifying agent. Non-limiting examples of the carriers comprise calcium carbonate, calcium phosphate, various sugars and starches, cellulose derivative, gelatine, vegetable oil and polyethylene glycol or the like. Other information regarding the carriers may be found in Remington: The Science and Practice of Pharmacy, 21st Ed., Lippincott, Williams & Wilkins (2005), of which the contents are incorporated herein by reference. The term "excipient" generally refers to the carrier, diluent and/or medium used to formulate effective pharmaceutical composition.

The term "administration" or "administrating" or the like refers to a method that enables a compound or composition to be delivered to a desired site of biological action. Such methods comprise but not limited to oral, parenteral (including intravenous, subcutaneous, intraperitoneal, intramuscular, intravascular injection or infusion), local, rectal administration or the like.

As for pharmaceutical or pharmacological active agent, the term "effective amount" refers to the amount of the medicament or agent which is not toxic but sufficient to achieve the desired effect. With respect to the oral formulation herein, the "effective amount" for an active substance in the composition refers to the amount required to achieve the desired effect in combination with another active substance in the composition. The effective amount may be determined individually and depends on the age and general condition of the receptor as well as specific active substance. The effective amount in specific case can be determined by a person skilled in the art through conventional test.

The term "active ingredient", "therapeutic agent", "active substance" or "active agent" refers to a chemical entity useful for treating or preventing target disorder, disease or condition effectively. The term herein may refer to for example the compound of formula I or salt thereof, the crystal form according to the invention or crystalline composition according to the invention.

In X-ray powder diffraction (XRPD or XRD) spectra, the diffraction pattern obtained from crystalline compound is generally characteristic for a particular crystal form in which the relative intensities of the bands (especially at low angles) may vary with the dominant orientation effect due to the difference of crystallization conditions, particle diameters, and other measuring conditions. Therefore, the relative intensities of diffraction peaks are not characteristic for the given crystal form. It is more important to note the relative positions of peaks rather than their relative intensities when determining whether the crystal form is the same as that known in the art. In addition, there may be slight errors in the positions of the peaks for any given crystal form, which is also well known in the art of crystallography. For example, the position of the peak may shift due to the change in temperature, sample movement or instrument calibration during analysis of the sample; and the measuring error of 2θ value may sometimes be about ±0.2°, typically about ±0.1°. Therefore, this error should be taken into account when determining the crystal structure. If the crystal forms according to the invention are described as substantially as shown in the figure, the term "substantially" is also intended to encompass such differences in the diffraction peak.

In the XRPD pattern, the peak position is usually represented by angle 2θ or crystal surface distance d and a simple conversion between d and θ is d=λ/2 sin θ, where d represents the crystal surface distance, λ represents the wavelength of the incident X-ray, and θ is diffraction angle. As for the same crystal form of the same compound, the peak positions of the XRPD pattern are similar as a whole, and the relative intensity error may be large. It should also be noted that, in identification of a mixture, some diffraction lines may be lost due to the factors like decrease in content, etc., and thus it is not necessary to rely on the entire bands observed in the high purity sample, and even one band may be characteristic for a given crystal.

In the present invention, X-ray powder diffraction pattern is determined as follows: apparatus: Bruker D8 ADVANCE X-ray diffractometer; method: target: Cu: K-Alpha; wavelength λ=1.54179 Å; voltage: 40 kV; current: 40 mA; scanning range: 4~40°; sample rotation speed: 15 rpm; scanning speed: 10°/min.

Differential scanning calorimetry (DSC) is used to measure the transition temperature when a crystal absorbs or releases heat due to changes in its crystal structure or crystal melting. The thermal transition temperature and the melting point error are typically within about 5° C., usually about 3° C. for the same crystal form of the same compound in a continuous analysis. When a compound is described as having a given DSC peak or melting point, it means the DSC peak or melting point ±5° C. Provided is an auxiliary method by DSC to identify different crystal forms. Different crystal forms may be identified according to their different transition temperature characteristics. It is noted that the DSC peak or melting point of the mixture may vary over a wide range. In addition, the melting temperature is associated with the rate of temperature rise due to the decomposition during the melting of the substance.

Differential scanning calorimetry (DSC) herein is measured by the following method: apparatus: TA Q2000 differential scanning calorimeter; method: a sample (~1 mg) is placed in a DSC aluminum pan, method: 25° C.~300° C., heating rate 10° C./min.

The crystal form according to the invention can also be characterized by cell parameters. Such parameters can be determined by single crystal X-ray crystallographic analysis. For example, the detailed information of cell parameters can be found in Chapter 3 of Stout & Jensen, X-Ray structure Determination: A Practical Guide, MacMillian Co., New York, N.Y. (1968).

The cell parameters herein are determined by the following method: Diffractometer: Rigaku MicroMax-007HF; Wavelength: 1.54178 Å; Temperature: 296K.

The term "crystalline composition" refers to a solid form, which comprise the crystal form A according to the invention. The amounts of the crystal form A contained in the crystalline composition may be 50% or more, 80% or more, 90% or more, or 95% or more. In addition to crystal form according to the invention, the crystalline composition may also optionally comprise other crystal or amorphous form of the compound of formula I or the salt thereof or the impurities other than these substances. It should be understood by those skilled in the art that the sum of contents of the components in the crystalline composition should be 100%.

Crystal Form A

Provided is crystal form A of the compound of formula I, which has diffraction peaks at 2θ=5.5°, 10.1°, 13.8°, 19.7°, 23.7°, 24.1°±0.2° in X-ray powder diffraction (XRPD) pattern.

In a specific embodiment, the crystal form A has diffraction peaks at 2θ=5.5°, 10.1°, 13.8°, 16.4°, 19.7°, 23.7°, 24.1°, 27.9°±0.2° in X-ray powder diffraction (XRPD) pattern.

In a more specific embodiment, the crystal form A has diffraction peaks at 2θ=5.5°, 10.1°, 13.8°, 16.4°, 17.9°, 19.0°, 19.7°, 20.3°, 21.8°, 22.1°, 23.7°, 24.1°, 25.5°, 27.9°, 32.9°, 34.0°±0.2° in X-ray powder diffraction (XRPD) pattern.

In a particular embodiment, diffraction peaks of the crystal form A of the compound of formula I are characterized as follows:

| Number | 2θ ± 0.2(°) | Relative intensity (%) |
| --- | --- | --- |
| 1 | 5.5 | 100.0 |
| 2 | 10.1 | 52.4 |
| 3 | 10.8 | 4.2 |
| 4 | 13.8 | 35.8 |
| 5 | 14.9 | 2.7 |
| 6 | 16.4 | 12.2 |
| 7 | 17.9 | 6.1 |
| 8 | 18.6 | 2.6 |
| 9 | 19.0 | 8.2 |
| 10 | 19.7 | 20.1 |
| 11 | 20.3 | 9.2 |
| 12 | 21.0 | 4.3 |
| 13 | 21.8 | 6.6 |
| 14 | 22.1 | 6.4 |
| 15 | 23.7 | 37.1 |
| 16 | 24.1 | 17.4 |
| 17 | 25.5 | 9.9 |
| 18 | 27.3 | 4.3 |
| 19 | 27.9 | 13.4 |
| 20 | 28.6 | 3.1 |
| 21 | 32.9 | 5.1 |
| 22 | 34.0 | 5.3 |

Figure 1:
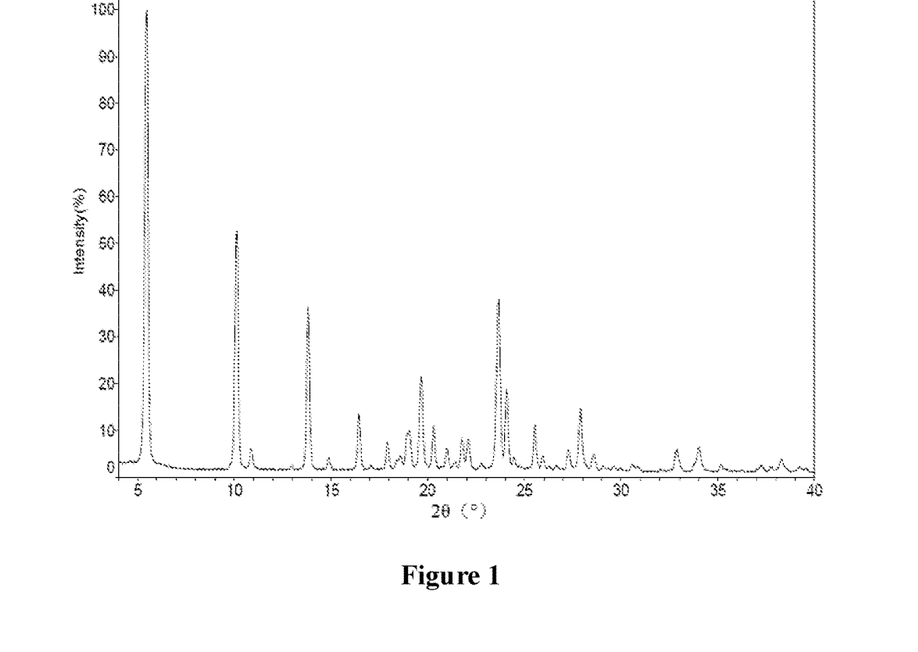
FIG. 1: XRPD pattern of the crystal form A of the compound of formula I.

In an embodiment, the X-ray powder diffraction pattern of the crystal form A of the compound of formula I is substantially shown in FIG. 1.

Figure 2:
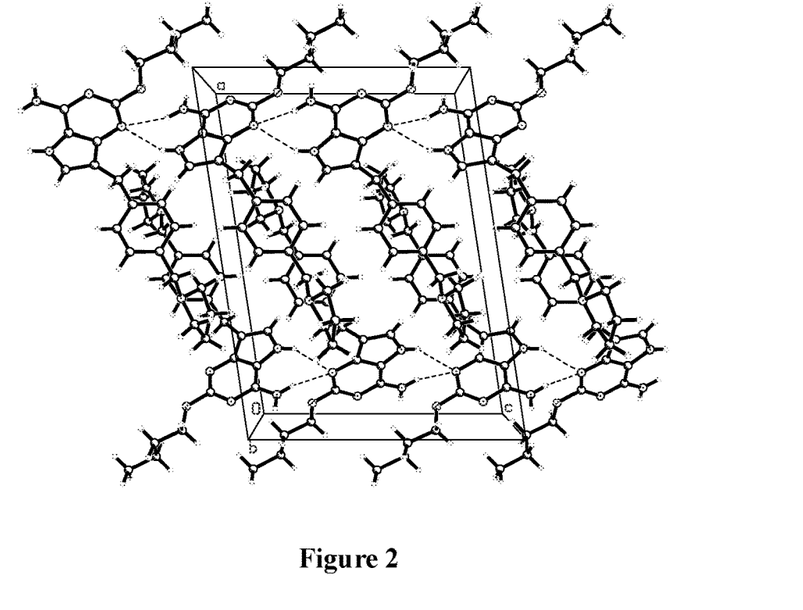
FIG. 2: Unit cell diagram of the crystal form A of the compound of formula I.

In another embodiment, the crystal form A of the compound of formula I has the following cell parameters (as shown in FIG. 2):
a=16.560 (3) Å
b=10.426 (2) Å
c=12.203 (2) Å
α=90°
β=98.54 (3°)
γ=90°
Space groups: P2$_1$/c
Z=4.

The crystal form A can also be characterized by DSC, with initial temperature of 199.0° C. and peak temperature of 200.4° C.

Figure 3:
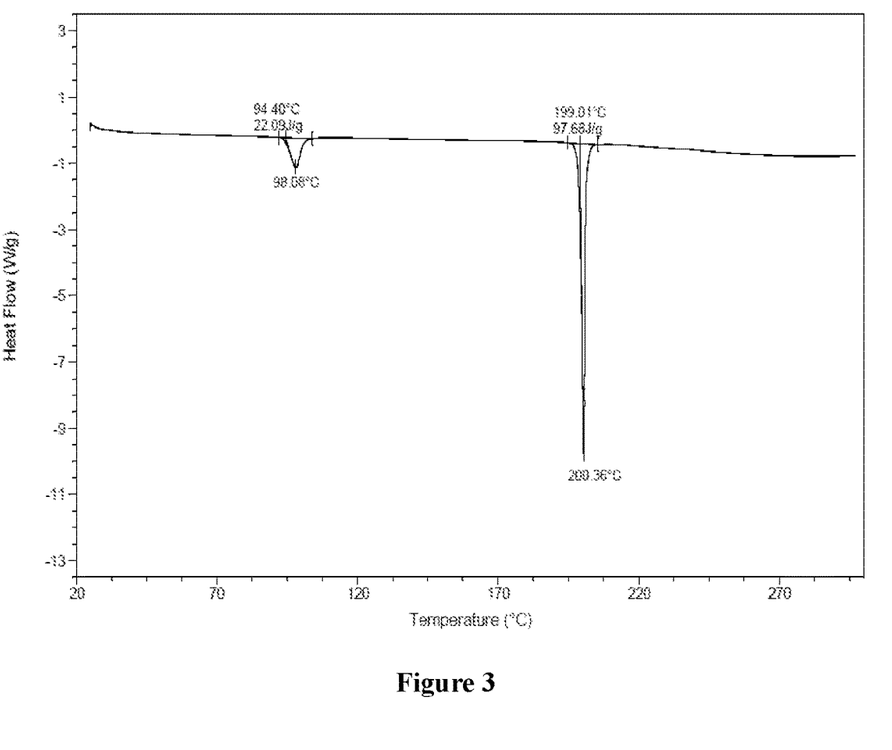
FIG. 3: DSC pattern of the crystal form A of the compound of formula I.

In an embodiment, DSC pattern of the crystal form A of the compound of formula I is shown in FIG. 3.

Preparation Process

Provided is also a process for preparing the crystal form A of the compound of formula I, comprising precipitating the crystal form A of the compound of formula I from a solvent.

In an embodiment, the process comprises the following steps:

1) dissolving the compound of formula I in a crystallizing solvent, which is preferably heated to promote dissolution; and 2) cooling for crystallization, filtrating, washing and drying to obtain the crystal form A.

In step 1), the crystallizing solvent is selected from the group consisting of methanol, ethanol, propanol, isopropanol, n-butanol, isobutanol, tertiary butanol, acetone, ethyl acetate, water and mixed solvent thereof; preferably ethanol.

In step 1), the amount of crystallizing solvent added per 1 g of the compound of formula I is 2 to 10 mL, preferably 4 to 8 mL, more preferably 5 to 7 mL.

In step 1), heating is used to form a homogeneous system of the compound of formula I and the crystallizing solvent. The heating temperature may be 40° C. to 90° C., preferably 50° C. to 80° C., more preferably 70° C. to 80° C.

Provided is also a crystalline composition, comprising the crystal form A of the compound of formula I. In an embodiment, based on the weight of the crystalline composition, the content of crystal form A is 50% or more, preferably 80% or more, more preferably 90% or more, and most preferably 95% or more. The crystalline composition, in addition to the crystal form A, can also comprise the compound of formula I or salt thereof in other crystal or amorphous forms, or impurities other than these substances.

Pharmaceutical Composition and Administration

Provided is a pharmaceutical composition, which comprises the crystal form A of the compound of formula I or the crystalline composition thereof in an effective amount. Furthermore, the pharmaceutical composition also may or may not comprise pharmaceutically acceptable carrier, excipient and/or medium.

The compound according to the invention is administrated in a pure form or in a suitable pharmaceutical composition form, which can be performed via any acceptable administration mode of the agent with similar use. Pharmaceutical composition according to the invention may be prepared by combining of the compound according to the invention or the salt thereof with a suitable pharmaceutically acceptable carrier, for example it may be formulated into solid, semi-solid, liquid or gas formulation, such as tablet, pill, capsule, powder, granule, ointment, emulsion, suspension, solution, suppository, injection, inhalant, gel, microsphere, aerosol or the like.

The pharmaceutical composition according to the invention may be prepared by the processes well-known in the art, such as conventional mixing, dissolution, granulation, dragee coating, levigation, emulsion, freeze-drying or the like.

Typical routes for administering the compound according to the invention or the pharmaceutical composition thereof comprise but not limited to oral, rectal, transmucosal, enteral administration or local, transcutaneous, inhalant, parenteral, sublingual, intravaginal, intranasal, intraocular, intraperitoneal, intramuscular, subcutaneous, intravenous administration.

In a preferred embodiment, the pharmaceutical composition is in an oral administration form. As for oral administration, the active compounds may be mixed with the pharmaceutically acceptable carriers, excipients and/or media well-known in the art to prepare the pharmaceutical composition. The carriers, excipients and media may be used to prepare the compounds according to the invention into tablet, pill, troche, dragee, capsule, liquid, gel, slurry, suspension or the like useful for oral administration to the patient.

Solid oral composition may be prepared by conventional mixing, filling or compressing processes, for example, by the following processes: mixing the active compound with solid excipients, optionally milling the resultant mixture, adding other proper adjuvants if necessary, and then processing the mixture into granules so as to obtain the core of tablet or dragee. The proper excipients comprise but not limited to filler, such as sugar, including lactose, sucrose, mannitol or sorbitol; cellulose preparation such as microcrystalline cellulose, maize starch, wheat starch, rice starch and potato starch; and other substances, such as silica gel, gelatin, tragacanth, methylcellulose, hydroxypropylmethyl cellulose, carboxymethyl cellulose sodium and/or polyvinylpyrrolidone; disintegrant, such as carboxymethyl starch sodium, croscarmellose sodium, crosslinked polyvinylpyrrolidone, agar or alginic acid. Salt such as sodium alginate may also be used. The core of the dragee may be optionally coated through well-known processes in general pharmaceutical practice, especially by enteric coating.

Beneficial Effects

The crystal form A of the compound of formula I according to the invention has the advantages of high purity, high crystallinity and good stability. Meanwhile, the preparation process of the crystal form A according to the invention is simple, the solvent is cheap and easily obtainable, the crystal form condition is mild, and the process is suitable for industrial production.

The technical solutions of the invention are illustrated according to the following paragraphs [1] to [20]:

[1] A crystal form A of the compound of formula I, characterized in that it has diffraction peaks at 2θ=5.5°±0.2°, 10.1°±0.2°, 13.8°±0.2°, 19.7°±0.2°, 23.7°±0.2°, 24.1°±0.2° in X-ray powder diffraction pattern.

[2] The crystal form A of the compound of formula I according to paragraph [1], characterized in that it has diffraction peaks at 2θ=5.5°±0.2°, 10.1°±0.2°, 13.8°±0.2°, 16.4°±0.2°, 19.7°±0.2°, 23.7°±0.2°, 24.1°±0.2°, 27.9°±0.2° in X-ray powder diffraction pattern.

[3] The crystal form A of the compound of formula I according to paragraph [2], characterized in that it has diffraction peaks at 2θ=5.5°±0.2°, 10.1°±0.2°, 13.8°±0.2°, 16.4°±0.2°, 17.9°±0.2°, 19.0°±0.2°, 19.7°±0.2°, 20.3°±0.2°, 21.8°±0.2°, 22.1°±0.2°, 23.7°±0.2°, 24.1°±0.2°, 25.5°±0.2°, 27.9°±0.2°, 32.9°±0.2°, 34.0°±0.2° in X-ray powder diffraction pattern.

[4] The crystal form A according to any one of paragraphs [1]-[3], characterized in that, it has X-ray powder diffraction pattern substantially shown in FIG. 1.

[5] The crystal form A according to any one of paragraphs [1]-[4], characterized in that, it has the following cell parameters:
a=16.560 (3) Å
b=10.426 (2) Å
c=12.203 (2) Å
α=90°

β=98.54 (3°)
γ=90°
Space groups: P2₁/c
Z=4.

[6] The crystal form A according to any one of paragraphs [1]-[5], characterized in that, when characterized by DSC, the initial temperature is 199.0° C.±5° C. and the peak temperature is 200.4° C.±5° C.

[7] A process for preparing the crystal form A according to any one of paragraphs [1]-[6], comprising the following steps:
 1) dissolving the compound of formula I in a crystallizing solvent, which is preferably heated to promote dissolution; and
 2) cooling for crystallization, filtrating, washing and drying to obtain the crystal form A.

[8] The preparing process according to paragraph [7], characterized in that the crystallizing solvent in step 1) is selected from the group consisting of methanol, ethanol, propanol, isopropanol, n-butanol, isobutanol, tertiary butanol, acetone, ethyl acetate, water and mixed solvent thereof.

[9] The preparing process according to paragraph [8], characterized in that the crystallizing solvent is ethanol.

[10] The preparing process according to any one of paragraphs [7]-[9], characterized in that, in step 1), the amount of crystallizing solvent added per 1 g of the compound of formula I is 2 to 10 mL.

[11] The preparing process according to paragraph [10], characterized in that the amount of crystallizing solvent added per 1 g of the compound of formula I is 4 to 8 mL.

[12] The preparing process according to paragraph [11], characterized in that the amount of crystallizing solvent added per 1 g of the compound of formula I is 5 to 7 mL.

[13] The preparing process according to any one of paragraphs [7]-[12], characterized in that, in step 1), heating is used to form a homogeneous system of the compound of formula I and the crystallizing solvent.

[14] The preparing process according to any one of paragraphs [7]-[13], characterized in that, in step 1), the heating temperature may be 40° C. to 90° C.

[15] The preparing process according to paragraph [14], characterized in that, in step 1), the heating temperature may be 50° C. to 80° C.

[16] The preparing process according to paragraph [15], characterized in that, in step 1), the heating temperature may be 70° C. to 80° C.

[17] A crystalline composition, characterized in that, based on the weight of the crystalline composition, the crystal form A of the compound of formula I according to any one of paragraphs [1]-[6] is 50% or more, preferably 80% or more, more preferably 90% or more, and most preferably 95% or more.

[18] A pharmaceutical composition, comprising the crystal form A according to any one of paragraphs [1]-[6] or the crystalline composition according to paragraph [17] in an effective amount.

[19] Use of the crystal form A of the compound of formula I according to any one of paragraphs [1]-[6] or the crystalline composition according to paragraph [17] or the pharmaceutical composition according to paragraph [18] for the manufacture of a medicament for treating Toll-like receptor 7 (TLR7) associated disease.

[20] The use according to paragraph [19], characterized in that the disease is virus infection, particularly the virus infection is hepatitis virus infection, for example hepatitis B or hepatitis C virus infection.

EXAMPLES

The following abbreviations are used herein: SEM-Cl: 2-(trimethylsilyl)ethoxymethyl chloride; SEM: 2-(trimethylsilyl)ethoxymethyl; DIPEA: diisopropylethylamine; TFA: trifluoroacetic acid; DMF: N,N-dimethylformamide; n-BuOH: n-butanol; NH₃.H₂O: aqueous ammonia; Na: sodium; XRPD: X-ray powder diffraction; DSC: differential thermal analysis.

The solvents used herein are commercially available and can be used without further purification. The synthesis reactions in preparation examples are generally performed under inert nitrogen atmosphere in anhydrous solvent. Data of proton magnetic resonance is recoded in Bruker Avance III 400 (400 MHz) spectrometer, with the chemical shift shown as (ppm) at tetramethylsilane low field. Mass spectrometry is determined on Agilent 1200 plus 6110 (&1956A). LC/MS or Shimadzu MS includes a DAD: SPD-M20A(LC) and Shimadzu Micromass 2020 detector. Mass spectrometer is equipped with an electrospray ionization (ESI) operated at positive or negative mode.

Preparation Example 1

Preparation of 2-butoxy-7-(4-(pyrrolidin-1-ylmethyl)benzyl)-5H-pyrrolo[3,2-d]pyrimidin-4-amine

Formula III: 2,4-dichloro-5-((2-(trimethylsilyl)ethoxy)methyl)-5H-pyrrolo[3,2-d]pyrimidine The compound of formula II (2,4-dichloro-5H-pyrrolo[3,2-d]pyrimidine) (4.00 kg, 21.28 mol) was dissolved in DMF (20.00 L), and DIPEA (2.58 kg, 20.00 mol) was added in portions at room temperature (25° C.) followed by stirring for 30 min. The reaction liquid was cooled to 0° C. with an ice bath, and then SEM-Cl (4.00 kg, 24.00 mol) was added dropwise slowly over 5 h at a dropping rate of 1 to 2 drops per second. After addition, the reaction liquid was stirred at 0° C. for 4 h. The reaction was monitored by HPLC. After completion, the reaction liquid was quenched and diluted with 70 L of water and then extracted with ethyl acetate (15 L×3). The combined organic phase was washed successively with 1 M aqueous hydrochloric acid (5 L×2) and saturated brine (7 L×2), and the solvent was removed by distillation under reduced pressure to give the compound of formula III (6.40 kg, 20.11 mol, yield 94.50%).

¹H NMR (400 MHz, DMSO-d₆) δ 8.24-8.35 (m, 1H), 6.70-6.85 (m, 1H), 5.77 (s, 2H), 3.45-3.57 (m, 2H), 0.74-0.86 (m, 2H), 0.00 (s, 9H).

Formula IV: 2-chloro-5-((2-(trimethylsilyl)ethoxy)methyl)-5H-pyrrolo[3,2-d]pyrimidin-4-amine The compound of formula III (1.60 kg, 5.03 mol) was dissolved in isopropanol (1.60 L) in a 10 L clave. Aqueous ammonia (4 L) was added at room temperature (25° C.) in one portion and the reaction mixture was stirred at 95° C. for 7 h. The reaction was monitored by HPLC. After completion, the reaction liquid was allowed to cool to room temperature and filtered through a Buchner funnel to give a dark brown solid. The solid was successively slurried with ethyl acetate/n-heptane (1/1, 5 L×2) and ethyl acetate (4 L) to give the compound of formula IV as brown solid (1.25 kg, 4.18 mol, yield 83.1%).

¹H NMR (400 MHz, DMSO-d₆) δ 7.61-7.77 (m, 1H), 6.97-7.19 (m, 2H), 6.28-6.38 (m, 1H), 5.54-5.67 (m, 2H), 3.43-3.53 (m, 2H), 0.76-0.91 (m, 2H), 0.07 (s, 9H).

Formula V: 2-butoxy-5-((2-(trimethylsilyl)ethoxy)methyl)-5H-pyrrolo[3,2-d]pyrimidin-4-amine To n-BuOH (17.0 L) was slowly added metal sodium (525.05 g, 22.84 mol) in portions under nitrogen. After addition, the temperature of the system was raised to 60° C., and stirring was performed continuously at the temperature until the metal sodium was completely dissolved. Then the system was cooled to 25° C., and the compound of formula IV (1.95 kg, 6.53 mol) was added in portions. After being mixed homogenously with stirring, the reaction mixture was continuously stirred for 8 h at 90° C. The reaction was monitored by HPLC. After completion, the reaction mixture was allowed to cool spontaneously to 25° C., and slowly poured into 30 L of saturated aqueous ammonium chloride. Then the reaction mixture was extracted with ethyl acetate (15 L×3) and the combined organic phase was washed with saturated brine (20 L×2), dried with anhydrous Na₂SO₄, and filtered. After the solvent was distilled off under reduced pressure, the residue was slurried in n-heptane (4 L) and the solid was separated by filtration and then slurried in ethyl acetate (5 L) to give the compound of formula V as yellow-white solid (1.53 kg, 4.55 mol, 69.7%).

¹H NMR (400 MHz, DMSO-d₆) δ 7.49-7.54 (m, 1H), 6.54-6.62 (m, 2H), 6.15-6.20 (m, 1H), 5.54 (s, 2H), 4.10-4.22 (m, 2H), 3.42-3.55 (m, 2H), 1.58-1.73 (m, 2H), 1.35-1.47 (m, 2H), 0.90-0.96 (m, 3H), 0.83-0.89 (m, 2H), 0.05 (s, 9H).

Formula VI: 2-butoxy-5H-pyrrolo[3,2-d]pyrimidin-4-amine

The compound of formula V (1.10 kg, 3.27 mol) was dissolved in TFA (5.50 L) and the reaction liquid was stirred at 25° C. for 16 h. The reaction was monitored by HPLC. After completion, TFA was removed by distillation under reduced pressure and the residue was dissolved in methanol (1.2 L) and ice water (1.2 L). pH of the system was adjusted to 12 with concentrated aqueous ammonia under uniform stirring. The mixture was stirred for 2 h and the precipitate was precipitated from the solution continuously. After filtration, the filter cake as white solid was slurried with 15% aqueous ammonia (1.2 L×3) and ethyl acetate (4 L) successively to give the compound of formula VI as white solid (550.00 g, 2.67 mol, 81.7%).

¹H NMR (400 MHz, methanol-d₄) δ 7.37 (d, J=2.89 Hz, 1H), 6.29 (d, J=3.01 Hz, 1H), 4.27 (t, J=6.53 Hz, 2H), 1.75 (d, J=7.91 Hz, 2H), 1.44-1.61 (m, 2H), 1.00 (t, J=7.40 Hz, 3H).

Formula VII: 4-((4-amino-2-butoxy-5H-pyrrolo[3,2-d]pyrimidin-7-yl)-hydroxymethyl)benzaldehyde

VII

To a three-necked flask were added terephthalaldehyde (790.64 mg, 5.82 mmol) and isopropanol (10 mL), 2-butoxy-5H-pyrrolo[3,2-d]pyrimidin-4-amine (1.00 g, 4.85 mmol) was added with stirring, and the system was cooled to 0° C. and stirred for another 10 min. Purified water (10 mL) and potassium carbonate (804.17 mg, 5.82 mmol) were added, and reacted at 25° C. for 16 h until the raw materials were depleted with the monitor by LCMS. Solid was precipitated out after the reaction was completed. After filtration, the resulting solid was slurried with 20 mL of purified water and 30 mL (ethyl acetate/n-heptane=1/20) successively, filtered and dried to give the compound of formula VII as yellow solid (1.50 g, 4.41 mmol, yield: 90.9%).

$^1$H NMR (400 MHz, methanol-$d_4$) δ 9.94 (s, 1H), 7.86 (d, J=8.16 Hz, 2H), 7.72 (d, J=8.16 Hz, 2H), 7.12-7.17 (m, 1H), 6.19 (s, 1H), 4.28 (t, J=6.53 Hz, 2H), 1.68-1.77 (m, 2H), 1.44-1.54 (m, 2H), 0.97 (t, J=7.34 Hz, 3H).

Formula VIII: (4-amino-2-butoxy-5H-pyrrolo[3,2-d]pyrimidin-7-yl)(4-(pyrrolidin-1-ylmethyl)phenyl)methanol To a 30 L clave were added the compound of formula VII (450.0 g, 1.32 mol) and isopropanol (4.5 L), and the mixture was stirred for 5 min. Then glacial acetic acid (119.0 g, 1.98 mol) was added and the temperature of the system was lowered to 0-10° C. with stirring. Pyrrolidine (112.4 g, 1.58 mol) was added dropwise, with the temperature below 10° C. After addition, sodium triacetoxyborohydride (420.0 g, 1.98 mol) was added in portions and reacted at 10-20° C. for 3 h until the raw materials were depleted with the monitor by liquid chromatography. After the completion of the reaction, 5 L of purified water was added and the temperature of the solution was lowered to about −10° C., and 12 L of 15% aqueous ammonia was added to the solution, with the solution temperature below 0° C. during addition. Solid was precipitated out under stirring. Filtration was performed and the resulting filter cake was slurried with 2 L of water and 2 L×2 ethyl acetate. Filtration was performed and drying was conducted under reduced pressure at 40° C. for 12 h to give the compound of formula VIII as yellow solid (465.0 g, 1.18 mol, yield 89.4%, moisture 0.9%).

$^1$H NMR (400 MHz, methanol-$d_4$) δ 7.46 (d, J=7.91 Hz, 1H), 7.29 (d, J=8.03 Hz, 1H), 7.09 (s, 1H), 6.12 (s, 1H), 4.29 (t, J=6.53 Hz, 2H), 3.60 (s, 2H), 2.52 (br. s., 4H), 1.66-1.83 (m, 6H), 1.49 (d, J=7.53 Hz, 2H), 0.98 (t, J=7.40 Hz, 3H).

Formula I: 2-butoxy-7-(4-(pyrrolidin-1-ylmethyl)benzyl)-5H-pyrrolo[3,2-d]pyrimidin-4-amine To 20 L clave were added the compound of formula VIII (440.0 g, 1.11 mol) and dichloromethane (7.0 L), and the temperature of the system was lowered to below −15° C. with stirring. After triethylsilane (880 mL, 5.55 mol) was added dropwise, trifluoroacetic acid (880 mL) was added dropwise, with the temperature kept below −10° C. during addition. After addition, the reaction was carried out at 0° C. for 2 h and monitored by liquid chromatography until the raw material point disappeared. After completion of the reaction, the reaction liquid was concentrated to dryness, and 2.2 L of ethyl acetate was added to the solution. Stirring was performed to lower the temperature to below 0° C. Then saturated sodium carbonate solution was added to adjust the solution to pH 9-10, during which the system temperature was kept below 10° C. Filtration was performed and the resulting filter cake was slurried with 2.2 L of water. Filtration was performed and drying was conducted under reduced pressure to give 550 g of trifluoroacetate of the compound of formula I as white solid.

To 1.6 L of ethanol was added 525 g of trifluoroacetate of the compound of formula I as white solid, and the temperature of the system was lowered to about 0° C. with stirring. Then 2.2 L of 1 mol/L sodium hydroxide solution was added. Filtration was performed and the resulting filter cake was slurried with 2.5 L of purified water. Filtration was performed and drying was conducted under reduced pressure to give 380.0 g of the compound of formula I as solid.

$^1$H NMR (400 MHz, methanol-d$_4$) δ 7.27 (d, J=8.0 Hz, 2H), 7.22 (d, J=8.0 Hz, 2H), 7.04 (s, 1H), 4.32 (t, J=6.6 Hz, 2H), 3.99 (s, 2H), 3.60 (s, 2H), 2.55-2.52 (m, 4H), 1.85-1.71 (m, 6H), 1.55-1.48 (m, 2H), 1.00 (t, J=7.4 Hz, 3H).

Example 1: Preparation of Crystal Form A of 2-butoxy-7-(4-(pyrrolidin-1-ylmethyl)benzyl)-5H-pyrrolo[3,2-d]pyrimidin-4-amine To ethanol (2.3 L) was added the compound of formula I (380 g) obtained in preparation example 1, and the mixture was heated reflux and stirred to be dissolved completely. After filtration, the filtrate was cooled to room temperature and allowed to stand for crystallization. Filtration was performed, and the obtained filter cake was dried under reduced pressure to give 310.0 g solid, i.e. crystal form A of the compound of formula I.

XRPD was measured as follows: apparatus: Bruker D8 ADVANCE X-ray diffractometer; method: target: Cu: K-Alpha; wavelength k=1.54179 Å; voltage: 40 kV; current: 40 mA; scanning range: 4~40°; sample rotation speed: 15 rpm; scanning speed: 10°/min.

The obtained compound crystal had diffraction peaks substantially as shown in FIG. 1.

Example 2: High Temperature Stability Test

The crystal form A of the compound of formula I was tested in the accelerated test under high temperature conditions for stability in accordance with *Guidelines for the Stability Test of Pharmaceutical Ingredients and Pharmaceutical Preparations* (Chinese Pharmacopoeia 2010 Appendix XIXC).

The crystal form A prepared in Example 1 was placed in an open-clean container at 60° C. The samples were taken for test on day 10, day 20 and day 30, respectively. The results were compared with the initial test result on day 0, and the results were shown in Table 1.

TABLE 1

| Sampling time (day) | Appearance | Content (%) | Total content of impurities (%) |
|---|---|---|---|
| 0 | White powder | 99.8 | 0.92 |
| 10 | Light yellow powder | 98.5 | 1.10 |
| 20 | Light yellow powder | 98.1 | 1.18 |
| 30 | Light yellow powder | 98.8 | 1.29 |

It was shown in high temperature stability test that, the crystal form A of the compound of formula I has good stability in high temperature conditions.

Example 3: High Humidity Stability Test

The crystal form A of the compound of formula I was tested in the accelerated test under high humidity conditions for stability in accordance with *Guidelines for the Stability Test of Pharmaceutical Ingredients and Pharmaceutical Preparations* (Chinese Pharmacopoeia 2010 Appendix XIXC).

The crystal form A prepared in Example 1 was subjected to an accelerated test in a constant temperature and humidity vessel under the conditions of 40° C./75% humidity (open). The samples were taken for test on day 30, day 60 and day 90, respectively. The results were compared with the initial test results on day 0, and the results were shown in the following Table 2.

TABLE 2

| Test conditions | Sampling time(day) | Appearance | Content (%) | Total content of impurities (%) |
|---|---|---|---|---|
| 40° C./75% humidity(open) | 0 | White powder | 100.2 | 0.92 |
| | 30 | White powder | 99.9 | 0.92 |
| | 60 | White powder | 99.9 | 0.65 |
| | 90 | White powder | 100.2 | 0.93 |

It was shown in high humidity stability test that, the crystal form A of the compound of formula I has good stability in high humidity conditions.

EXAMPLES OF PHARMACEUTICAL ACTIVITY

Efficacy Example 1: Toll-Like Receptor 7 and Toll-Like Receptor 8 In Vitro Receptor Binding Activity Screen Reagents:

HEK-blue hTLR7 cell and HEK-blue hTLR8 cell (available from InvivoGen)

DMEM medium heat inactivated fetal bovine serum

Anti *Mycoplasma* reagent Normocin™ bleomycin blasticidin

The structure of GS-9620 and R848 used are as follows, wherein the preparation of GS-9620 could be referred to the process disclosed in US20100143301; R848 was commercially available from ABGENT (IMG-2208, specification: 0.5 mg).

GS9620

R848/Resiquimod

Scheme:

1. Preparation of 96-well compound plate:

The compounds were gradient diluted with DMSO in 3-fold using liquid work station POD starting at a concentration of 10 mmol/L and 10 points were diluted (2nd column to 11th column, and each point was duplicated). At 12th column, 1 μL of 5 mg/mL positive compound R848 was added as positive control; and at 1st column, 1 μL of DMSO was added as negative control. Each well contained 1 μL of DMSO.

2. The cells in culture flask were collected and the cell density was diluted to 250,000 cells/mL.

3. 200 μL (50,000 cells/well) of cell suspension was added into prepared compound plate and the final concentration of DMSO in each well was 0.5%.

4. The culture plates containing cells and the compounds were incubated in $CO_2$ incubator for 24 h at 37° C., 5% $CO_2$.

5. After 24 h incubation, 20 μL of supernatant was removed from each well to a 96-well transparent assay plate. To each well of the assay plate was added 180 μL of Quanti-Blue reagent and the plate was incubated in an incubator at 37° C., 5% $CO_2$ for 1 h.

6. After 1 h, the content of alkaline phosphatase in 20 μL of supernatant was determined using Microplate Reader OD650.

7. $EC_{50}$ of each compound was obtained with Prism software.

Results were shown in Table 3.

TABLE 3

| Name of the compound | TLR7 EC50 (nM) | TLR8 EC50 (nM) |
|---|---|---|
| GS-9620 | 517 | 7867 |
| Compound of formula I | 160 | 11632 |

The compound of formula I according to the invention showed higher in vitro receptor binding activity to Toll-like receptor 7 than the control (Toll-like receptor 7 agonist GS-9620) and lower in vitro receptor binding activity to Toll-like receptor 8 than the control (Toll-like receptor 7 agonist GS-9620). The compound of the present invention has distinct selectivity differences with respect to different receptors, and the effect is superior over the prior art.

Efficacy Example 2: Peripheral Blood Mononuclear Cell Test Scheme

The purpose of this example is to determine the expression level of cytokines 24 h after stimulation to human peripheral blood mononuclear cells (PBMC) with the compound of formula I.

The cell supernatant was assayed without dilution and the levels of IFN-α were directly determined. The compound of formula I was firstly formulated into 20 mM DMSO stock solution during the test and was gradient diluted with cell medium in 10-fold with the total number of 11 diluting points. The compounds in 9 diluting points (the highest concentration was 200 μmol/L) were added into 96-well plate with 50 μL in each well. Fresh human peripheral blood mononuclear cells were inoculated, with 150 μL in each well containing 450,000 cells. The cell culture plate was incubated in an incubator at 37° C., 5% $CO_2$ for 24 h. After incubation, the culture plate was centrifuged at 1200 rpm for 5 min and the supernatant was collected and stored at −20° C. for determination. The determination of cytokine was performed using Cytometric Bead Array (CBA) of BD-Pharmingen on flow cytometer. Using the above determining method, the lowest drug concentration stimulating the production of 30 pg/mL of IFN-α was designated as the MEC value in the cytokine stimulating test. The results were shown in Table 4.

TABLE 4

| Name of the compound | IFN-α MEC(nM) | TNF-α MEC (nM) |
|---|---|---|
| GS-9620 | 50 | 500 |
| Compound of formula I | 5 | 500 |

Compared with the control (GS-9620), the compound of formula I of the invention showed better in vitro IFN-α inducing activity of PBMCs and comparable TNF-α inducing activity.

SEQUENCE LISTING

Not Applicable

The invention claimed is:

1. A crystal form A of a compound of formula I:

wherein the crystal form A is characterized by an X-ray powder diffraction pattern having diffraction peaks (2θ) at 5.5°±0.2°, 10.1°±0.2°, 13.8°±0.2°, 19.7°±0.2°, 23.7°±0.2°, and 24.1°±0.2°.

2. The crystal form A according to claim 1, wherein the crystal form A is further characterized by a differential scanning calorimetry thermogram having an initial temperature of 199.0° C.±5° C. and a peak temperature of 200.4° C.±5° C.

3. A composition comprising a carrier or excipient and at least 95% w/w of the crystal form A according to claim 1, based on a total weight of the composition.

4. A composition comprising a carrier or excipient and at least 90% w/w of the crystal form A according to claim 1, based on a total weight of the composition.

5. A composition comprising a carrier or excipient and at least 80% w/w of the crystal form A according to claim 1, based on a total weight of the composition.

6. A composition comprising a carrier or excipient and at least 50% w/w of the crystal form A according to claim 1, based on a total weight of the composition.

7. The composition according to claim 6, wherein the carrier or excipient is a pharmaceutically acceptable carrier or excipient.

8. A pharmaceutical composition comprising a pharmaceutically acceptable carrier or excipient and a therapeutically effective amount of the crystal form A according to claim 1.

9. A method for inhibiting toll-like receptor activity in a subject, wherein the method comprises administering to the subject in need thereof a therapeutically effective amount of the crystal form A according to claim 1.

10. The method according to claim 9, wherein the subject has a viral infection.

11. A method for inhibiting toll-like receptor activity in a subject, wherein the method comprises administering to the subject in need thereof a therapeutically effective amount of the composition according to claim 6.

12. The method according to claim 11, wherein the subject has a viral infection.

13. A method for inhibiting toll-like receptor activity in a subject, wherein the method comprises administering to the subject in need thereof a therapeutically effective amount of the pharmaceutical composition according to claim 8.

14. The method according to claim 13, wherein the subject has a viral infection.

15. A process for preparing the crystal form A according to claim 1, wherein the process comprises the following steps:
   1) dissolving the compound of formula I according to claim 1 in a crystallizing solvent to form a solution, wherein the crystallizing solvent is selected from the group consisting of methanol, ethanol, n-propanol, isopropanol, n-butanol, isobutanol, tert-butanol, acetone, ethyl acetate and water, or a co-solvent mixture of any two or more thereof;
   2) heating the solution of step 1) to reflux while stirring;
   3) cooling the solution of step 2) to room temperature;
   4) filtering the solution of step 3) to obtain a filter cake; and
   5) drying the filter cake of step 4) to obtain the crystal form A according to claim 1.

16. The process according to claim 15, wherein the crystallizing solvent in step 1) is ethanol.

17. The process according to claim 15, wherein in step 1), the amount of crystallizing solvent added per gram of the compound of formula I is 2 mL to 10 mL.

18. The process according to claim 15, wherein in step 1), the amount of crystallizing solvent added per gram of the compound of formula I is 4 mL to 8 mL.

19. The process according to claim 15, wherein in step 1), the amount of crystallizing solvent added per gram of the compound of formula I is 5 mL to 7 mL.

20. A crystal form A of a compound of formula I:

wherein the crystal form A is characterized by an X-ray powder diffraction pattern having diffraction peaks (2θ) at 5.5°±0.2°, 10.1°±0.2°, 13.8°±0.2°, 19.7°±0.2°, 23.7°±0.2°, and 24.1°±0.2°; and further wherein the crystal form A has the following cell parameters:
a=16.560 (3) Å;
b=10.426 (2) Å;
c=12.203 (2) Å;
α=90°;
β=98.54 (3°);
γ=90°;
Space group P2$_1$/c; and
Z=4.

* * * * *